Figure 1:
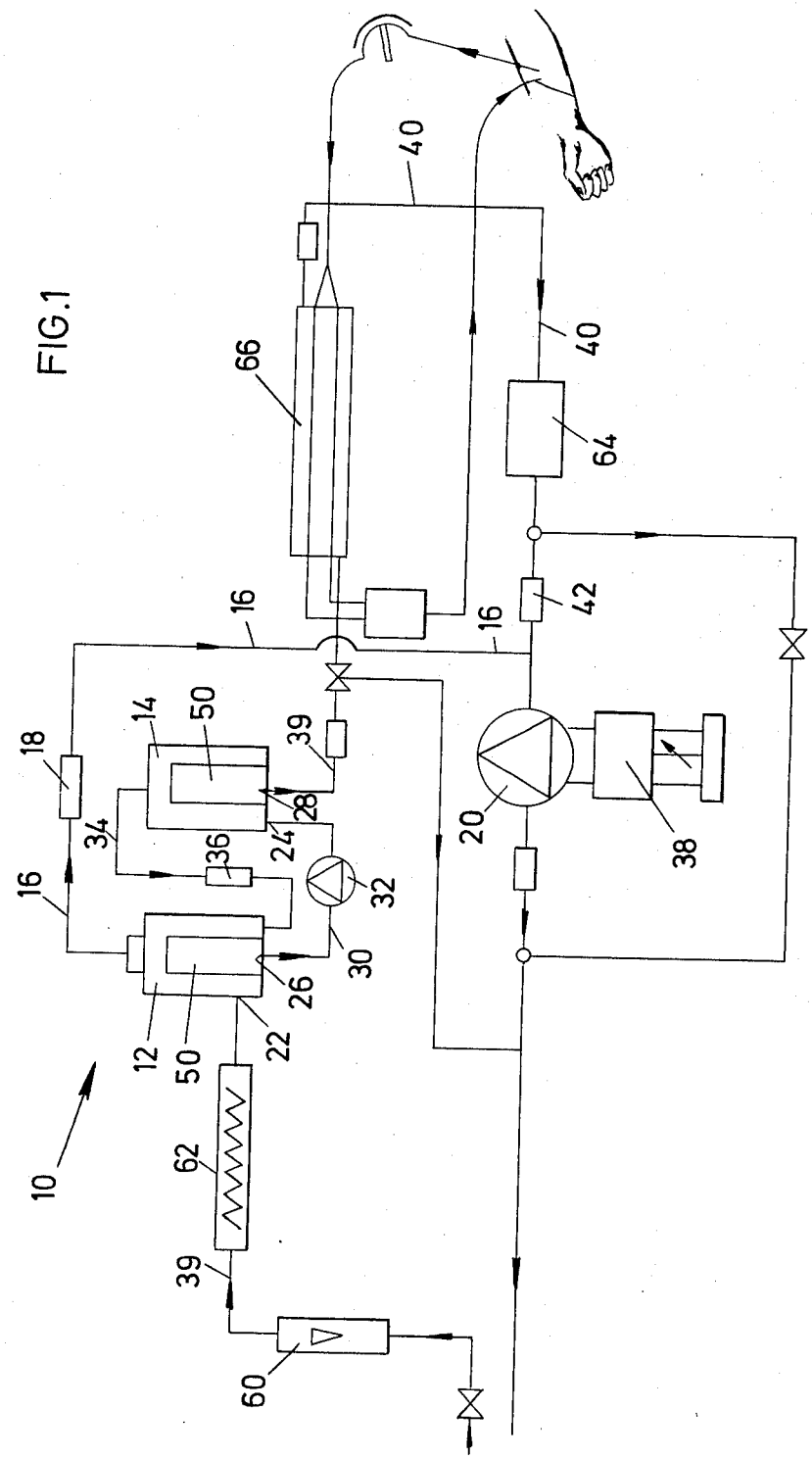

United States Patent [19]

Sama

[11] 3,970,438

[45] July 20, 1976

[54] DEAERATING ARRANGEMENT FOR DIALYZER

[75] Inventor: Claudio Sama, Mirandola, Italy

[73] Assignee: Sandoz Ltd., Basel, Switzerland

[22] Filed: Nov. 11, 1974

[21] Appl. No.: 522,896

[30] Foreign Application Priority Data
Nov. 15, 1973 Italy .................................. 40103/73

[52] U.S. Cl. .................................. 55/190; 55/195; 55/200
[51] Int. Cl.² ........................................ B01D 19/00
[58] Field of Search .................. 55/36, 41, 55, 159, 55/190, 192, 195, 199, 200; 210/22, 188, 321

[56] References Cited
UNITED STATES PATENTS

| | | | |
|---|---|---|---|
| 2,989,143 | 6/1961 | Hallstrom | 55/55 X |
| 3,056,503 | 10/1962 | Roosa | 210/436 X |
| 3,626,670 | 12/1971 | Pecker | 210/321 X |
| 3,744,636 | 7/1973 | Commarmot | 210/321 X |
| 3,827,561 | 8/1974 | Serfass et al. | 210/321 X |

Primary Examiner—Charles N. Hart
Assistant Examiner—Richard W. Burks
Attorney, Agent, or Firm—Gerald D. Sharkin; Robert S. Honor; Walter F. Jewell

[57] ABSTRACT

The invention concerns a novel deaerating arrangement for deaerating dialysis liquid in dialysis equipment of the type comprising a dialysis liquid feed line leading to a dialysis device and a dialysis liquid take off line leading from the dialysis device, wherein the deaerating arrangement comprises at least one deaerating chamber having a dialysis liquid inlet and dialysis liquid outlet in the dialysis liquid feed line, and a deaerating line which leads off from the head of the deaerating chamber through a first liquid flow rate restrictor to an evacuation pump which, in operation, creates a negative pressure in the deaerating chamber and withdraws air or gas formed in said deaerating chamber.

3 Claims, 2 Drawing Figures

DEAERATING ARRANGEMENT FOR DIALYZER

This invention relates to a deaerating arrangement for deaerating dialysis liquid in dialysis equipment of the type comprising a dialysis liquid feed line leading to a dialysis device, such as an artificial kidney of the Kiil or Kolff type, and a dialysis liquid take off line leading from said dialysis device.

In accordance with the invention, the above deaerating arrangement comprises at least one deaerating chamber having a dialysis liquid inlet and dialysis liquid outlet in the dialysis liquid feed line, and a deaerating line which leads off from the head of the deaerating chamber through a first liquid flow rate restrictor to an evacuation pump which, in operation, creates a negative pressure in the deaerating chamber and withdraws air or gas formed in said deaerating chamber.

A pair of deaerating chambers may be provided in series in the dialysis liquid feed line, the dialysis liquid outlet of the deaerating chamber first in series then leading to the dialysis liquid inlet of the deaerating chamber second in the series. A feed back line leading from the head of the deaerating chamber second in series back to the deaerating chamber first in series through a second liquid flow rate restrictor may then be provided. Thus, the negative pressure created in the deaerating chamber first in series is transferred to the deaerating chamber second in series and air or gas formed in the deaerating chamber second in series is thereby withdrawn into the deaerating chamber first in series.

In the deaerating arrangement comprising a pair of deaerating chambers such as described above, a dialysis liquid biassing pump may be provided between the dialysis liquid outlet of the deaerating chamber first in series and the dialysis liquid inlet of the deaerating chamber second in series.

The evacuation pump employed for creating a negative pressure in the one or more deaerating chambers may conveniently be provided with adjustment means for adjusting its pumping capacity and thus the negative pressure in the one or more deaerating chambers. The so-called evacuation pump may be an ultra-filtration pump regularly employed in dialysis equipment. The evacuation pump is then the ultra-filtration pump which is incorporated in the dialysis liquid take off line leading from the dialysis device. In order to ensure that the deaerating line is connected to a point of lowest pressure in the dialysis liquid line, the deaerating line may then be connected to the dialysis liquid take off line upstream from the evacuation or ultra-filtration pump and downstream from a third liquid flow rate restrictor provided in the dialysis liquid take off line.

The first liquid flow rate restrictor may comprise a capillary tube and, similarly, in an arrangement involving a pair of deaerating chambers, the second liquid flow rate restrictor may also comprise a capillary tube. The capillary tubes are dimensioned to allow only small quantities of liquid to flow, but, of course, to allow gas flow without hinderance. The third liquid flow rate restrictor provided upstream from the point of connection of the deaerating line to the dialysis liquid take off line may comprise a bottle-neck dimensioned to create a pressure drop in the dialysis liquid take off line between a point upstream of the bottle-neck and a point downstream of the bottle-neck. As already mentioned, the bottle-neck functions to ensure that the pressure at the point of connection of the deaerating line to the dialysis liquid take off line is lower than at any other point in the dialysis liquid lines.

The one or more deaerating chambers may comprise a cylindrical housing having a base end into and from which the dialysis liquid inlet and dialysis liquid outlet pass and having a head end from which the deaerating line leads, a cylindrical divider chamber dividing said dialysis liquid inlet from said dialysis liquid outlet mounted inside the cylindrical housing on said base and over said dialysis liquid outlet and terminating short of said head end, and a foraminous mass located in the volume defined between the cylindrical housing and the cylindrical divider chamber to encourage bubble formation under the negative pressure created by the evacuation pump as dialysis liquid passes through the dialysis liquid inlet into the deaerating chamber upwardly through the foraminous mass and then downwardly in the cylindrical divider chamber to the dialyser liquid outlet. The foraminous mass located in the volume defined between the cylindrical housing and the cylindrical divider chamber may conveniently comprise a mesh structure of metal and plastics material which may be wound about the cylindrical divider chamber.

The invention extends also to dialysis equipment of the type comprising a dialysis liquid feed line leading to a dialysis device and a dialysis liquid take off line leading from the dialysis device, which incorporates a deaerating arrangement such as described above.

The invention will now be described with reference to the accompanying drawings showing by way of example, a particular embodiment of the invention.

Figure 2:
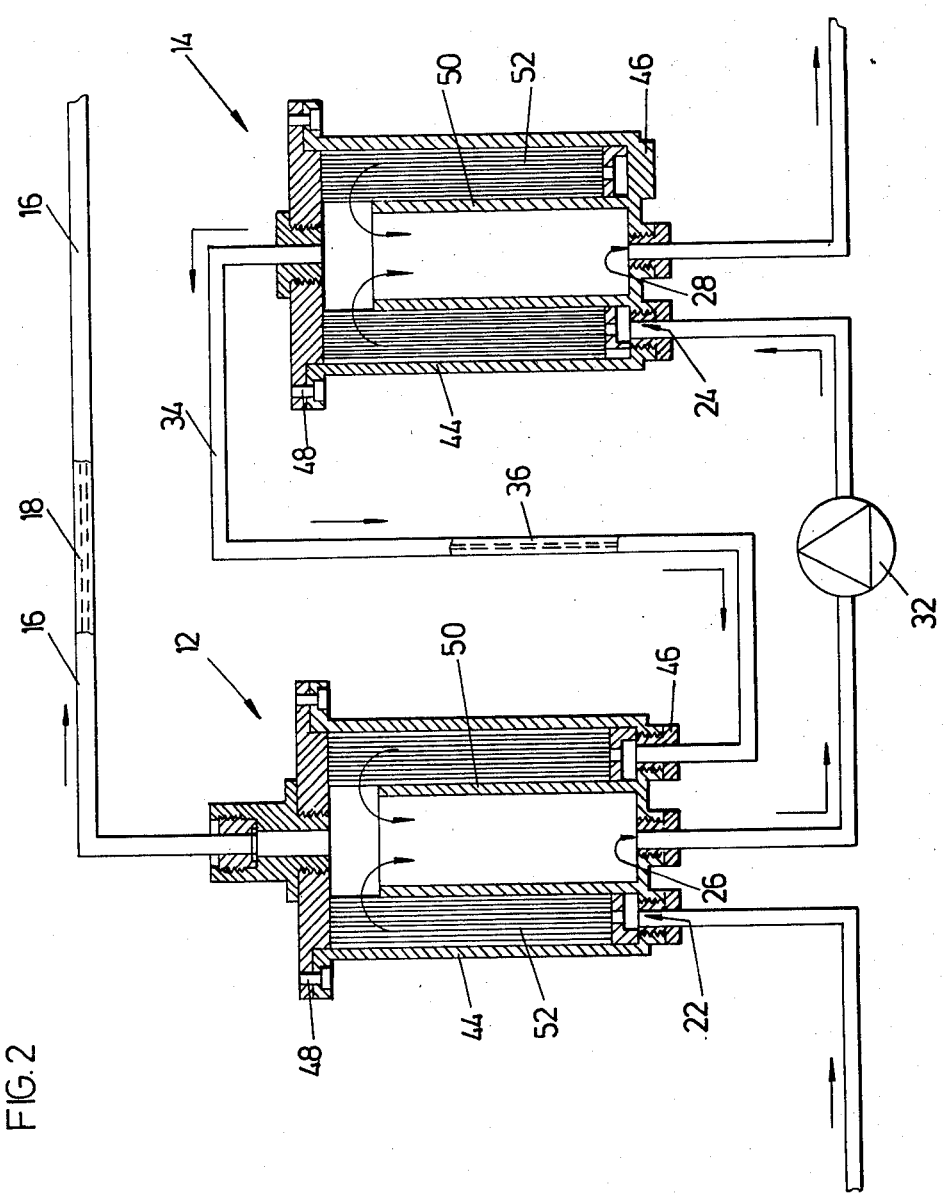

In the drawings:

FIG. 1 shows a schematic representation of dialysis equipment incorporating a deaerating arrangement of the invention;

FIG. 2 shown an enlarged cross-section of a pair of deaerating chambers with associated dialyser liquid lines and deaerating lines.

Referring to FIG. 1 of the drawings, the dialysis equipment incorporates a deaerating arrangement referred to, generally by reference numeral 10, in the dialysis liquid inlet line referred to by reference numeral 39. The deaerating arrangement comprises a pair of deaerating chambers 12 and 14, a deaerating line 16 leading off from the head of the deaerating chamber 12 through a first liquid flow rate restrictor 18, namely a capillary, to an evacuation pump 20. In operation, the pump 20 creates a negative pressure in the deaerating chambers 12 and 14 and withdraws air or gas formed in said deaerating chambers. The deaerating chambers each have a dialysis liquid inlet 22 and 24 respectively, and a dialysis liquid outlet 26 and 28 respectively. The liquid outlet 26 of the deaerating chamber 12 first in series leads via conduit 30 and biassing pump 32 to a dialysis liquid inlet 24 of the deaerating chamber 14 second in series. A feed back line 34 leads from the head of the deaerating chamber 14 second in series back to the deaerating chamber 12 first in series through a second liquid flow rate restrictor 36, again in the form of a capillary. In this manner, negative pressure created in the deaerating chamber 12 by the evacuation pump 20 is transferred to the deaerating chamber 14, and air or gas formed in the deaerating chamber 14, i.e. that second in series, is thereby withdrawn into the deaerating chamber 12, i.e. the one first in series. In this construction, as already mentioned, a dialysis liquid biassing pump 32 is provided between the dialysis liquid outlet 26 of the deaerating chamber 12 and the dialysis liquid inlet 24 of the deaerating chamber 14.

In the construction shown in FIG. 1, the evacuation pump 20 employed for creating a negative pressure at the head of the deaerating chamber 12 is provided with adjustment means 38 for adjusting its pumping capacity and thus the negative pressure in the deaerating chambers 12 and 14. The evacuation pump 20 in the embodiment shown constitutes an ultra-filtration pump which is incorporated in the dialysis liquid take off line referred to by reference numeral 40. In order to ensure that the deaerating line 16 is connected to a point of lowest pressure in the dialysis liquid line, the deaerating line 16 is connected to the dialysis liquid take off line 40 upstream from the evacuation or ultra-filtration pump 20, and downstream from a third liquid flow rate restrictor 42, in the form of a bottle-neck, provided in the dialysis liquid take off line 40.

It will be appreciated that the capillary tubes 18 and 36 are dimensioned to allow only small quantities of liquid to flow, but to allow gas flow without hinderance. Similarly, the bottle-neck employed as the third flow rate restrictor 42 is dimensioned to create a pressure drop in the dialysis liquid take off line 40 between a point upstream of the bottle-neck and a point downstream of the bottle-neck.

Referring now particularly to FIG. 2 of the drawings, the deaerating chambers each comprise a cylindrical housing 44 having a base end 46 into and from which the dialysis liquid inlets 22 and 24 and dialysis liquid outlets 26 and 28 pass and having a head end 48 from which the deaerating lines 16 and 34 lead. A cylindrical divider chamber 50 divides the dialysis liquid inlets 22 and 24 from the dialysis liquid outlets 26 and 28 by being mounted inside the cylindrical housing 44 on said base ends 46 over the dialysis liquid outlets 26 and 28. The divider chambers 50 terminate short of the head ends 48. A foraminous mass 52, conveniently of metal or plastics mesh material wound about the divider chambers 50, is located in the volume divided between the cylindrical housings 44 and the cylindrical divider chambers 50. The foraminous mass is provided to encourage bubble formation under the negative pressure created by the evacuation or ultra-filtration pump 20 as dialysis liquid passes through the dialysis liquid inlets 22 and 24 into the deaerating chambers 12 and 14 upwardly through the foraminous mass 52 and then downwardly in the divider chambers 50 to the dialyser liquid outlets 26 and 28.

Reference numerals 60 and 62 at the top left-hand side of FIG. 1 refer to a flow meter and thermostatically controlled dialysis liquid heater respectively. The reference numeral 64 at the bottom right-hand side refers to a blood leak detector, and reference numeral 66 at the top right-hand side refers to a dialysis device.

Operation of the deaerating arrangement of the invention and dialysis equipment involving such deaerating arrangement would be readily appreciated by those of ordinary skill in the art of dialysis. Similarly, the need for a deaerating arrangement in dialysis equipment will be readily appreciated.

I claim:

1. A deaerating arrangement for deaerating dialysis liquid in dialysis equipment of the type comprising a dialysis liquid feed line leading to a dialysis device and a dialysis liquid take-off line leading from the dialysis device, wherein the deaerating arrangement comprises a pair of deaerating chambers provided in series in the dialysis liquid feed line, the dialysis liquid outlet of the deaerating chamber first in series then leading to the dialysis liquid inlet of the deaerating chamber second in series, a feed back line leading from the head of the deaerating chamber second in series back to the base end of the deaerating chamber first in series through a first liquid flow-rate restrictor then being provided a deaerating line which leads off from the head of the deaerating chamber first in series through a second liquid flow-rate restrictor to an evacuation pump which, in operation, creates a negative pressure in the deaerating chamber first in series and withdraws air or gas formed in said first in series deaerating chamber, whereby the negative pressure created in the deaerating chamber first in series is transferred to the deaerating chamber second in series and whereby air or gas formed in the deaerating chamber second in series is withdrawn into the deaerating chamber first in series, the deaerating chamber further comprising a cylindrical housing having a base end into and from which the dialysis liquid inlet and dialysis liquid outlet pass and having a head end from which the deaerating line leads, a cylindrical divider chamber dividing said dialysis liquid inlet from said dialysis liquid outlet mounted inside the cylindrical housing on said base end over said dialysis liquid outlet and terminating short of said head end, and a foraminous mass located in the volume defined between the cylindrical housing and the cylindrical divider chamber to encourage bubble formation under the negative pressure created by the evacuation pump as dialysis liquid passes through the dialysis liquid inlet into the deaerating chamber upwardly through the foraminous mass and then downwardly in the cylindrical divider chamber to the dialyser liquid outlet.

2. A deaerating arrangement according to claim 1, wherein a dialysis liquid biassing pump is provided between the dialysis liquid outlet of the deaerating chamber first in series and the dialysis liquid inlet of the deacrating chamber second in series.

3. A deaerating arrangement according to claim 1, wherein the evacuation pump is incorporated in the dialysis liquid take off line leading from the dialysis device, the deaerating line then being connected to the dialysis liquid take off line upstream from the evacuation pump and downstream from a third liquid flow rate restrictor provided in the dialysis liquid take off line.

* * * * *